United States Patent
Perregaard et al.

(10) Patent No.: US 6,436,940 B2
(45) Date of Patent: Aug. 20, 2002

(54) INDANE OR DIHYDROINDOLE DERIVATIVES

(75) Inventors: Jens Kristian Perregaard, Jaegerspris; Ivan Mikkelsen, Koge; Henrik Pedersen, Bronshoj, all of (DK)

(73) Assignee: H. Lundbeck A/S, Copenhagen (DK)

( * ) Notice: Subject to any disclaimer, the term of this patent is extended or adjusted under 35 U.S.C. 154(b) by 0 days.

(21) Appl. No.: 09/915,680

(22) Filed: Jul. 26, 2001

Related U.S. Application Data

(62) Division of application No. 09/331,557, filed as application No. PCT/DK97/00588 on Dec. 19, 1997, now Pat. No. 6,331,544.

(30) Foreign Application Priority Data

Dec. 20, 1996 (DK) .............................................. 1469/96
Dec. 19, 1997 (WO) ................................ PCT/DK97/00588

(51) Int. Cl.[7] .................... A61K 31/496; C07D 405/14; C07D 409/14
(52) U.S. Cl. ............................ 514/254.09; 514/217.05; 514/252.19; 514/253.09; 514/254.03; 514/254.04; 514/254.07; 540/598; 544/295; 544/364; 544/367; 544/369; 544/370; 544/373
(58) Field of Search ................................. 544/373, 295, 544/364, 367, 369, 370; 514/254.09, 217.05, 252.19, 253.09, 254.04, 254.03, 254.07; 540/598

(56) References Cited

U.S. PATENT DOCUMENTS 5,532,241 A * 7/1996 Bottcher et al. ............ 514/254
5,753,662 A 5/1998 Peglion et al. ............... 514/254

FOREIGN PATENT DOCUMENTS

| EP | 0 574 313 | 12/1993 | ......... C07D/409/12 |
| WO | WO 95/33721 | 12/1995 | ......... C07D/211/18 |

OTHER PUBLICATIONS

Saxena, *Pharmac. Ther.* 66: 339–368 (1995).
TenBrink et al., *J. Med. Chem.* 39: 7435–7437 (1996).

* cited by examiner

*Primary Examiner*—Emily Bernhardt
(74) *Attorney, Agent, or Firm*—Darby & Darby

(57) ABSTRACT

The present invention relates to substituted indane or dihydroindole compounds of

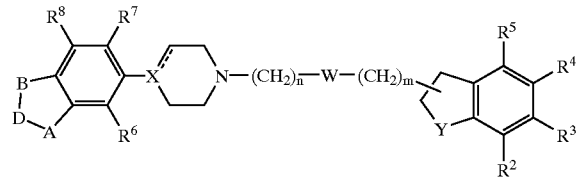

Formula (I), wherein A and B are independently O or S; D is an optionally substituted methylene group; X is N or optionally substituted C; and W is a spacer group. The compounds are either selective dopamine D4 ligands or they have combined effects at dopamine D4 and serotonergic receptors and/or the serotonergic transporter. These compounds are therefore useful in the treatment of certain psychiatric and neurologic disorders, including psychosis, depression and anxiety.

19 Claims, No Drawings

US 6,436,940 B2

INDANE OR DIHYDROINDOLE DERIVATIVES

This is a division of application Ser. No. 09/331,557, filed Aug. 3, 1999 now U.S. Pat. No. 6,331,544, which is a 371 PCT/DK97/00588 filed Dec. 19, 1997. The prior application is hereby incorporated herein by reference, in its entirety.

FIELD OF THE INVENTION

The present invention relates to a novel class of substituted indane or dihydroindole compounds having effects at dopamine $D_4$ receptors. The compounds are either selective dopamine $D_4$ ligands or they have combined effects at dopamine $D_4$ and serotonergic receptors and/or the serotonergic transporter. These compounds are therefore useful in the treatment of certain psychiatric and neurologic disorders, including psychosis, depression and anxiety.

BACKGROUND OF THE INVENTION

Related compounds are known from WO patents Nos. WO 9421627-A1, WO 9421630-A1, WO 94 21626-A1 describing various series of indolyl- or indazolylmethyl piperidine or piperazine derivatives as selective dopamine $D_4$ antagonists. No data are given. The compounds are only said to give $K_i$ values of less than 1.5 $\mu$M in a test for displacement of 3H spiperone from human dopamine $D_4$ receptor subtypes in clonal cell lines.

EP patent No. 574313 A1 describes compounds with piperidine, tetrahydropyridine, or piperazine rings substituted in position 1 and 4 with various aryl or heteroaryl groups, including certain 1-(indane or indanemethyl) piperidine, tetrahydropyridine, or piperazine derivates substituted in the 4-position with 1,4-benzodioxane. The compounds are claimed to have effects at dopamine $D_2$ and $D_4$ receptors.

Dopamine $D_4$ receptors belong to the dopamine $D_2$ receptor family considered to be responsible for antipsychotic effects of neuroleptics. Furthermore, dopamine $D_4$ receptors are primarily located in areas of the brain other than striatum (Van Tol, et al. *Nature*, 1991, 350, 610), the low level in striatum suggesting lack of extrapyramidal activity. Also, dopamine $D_4$ receptor levels have been reported to be elevated in schizophrenic patients (Seeman et al., *Nature*, 1993, 365, 441.) and the antipsychotic clozapine which is lacking extrapyramidal side effects, has a high affinity for dopamine $D_4$ receptors (Van Tol, et al. *Nature*, 1991, 350, 610.)

Various effects are known with respect to compounds which are ligands at the different serotonin receptor subtypes. As regards the 5-HT$_{2A}$ receptor which was previously referred to as the 5-HT$_2$ receptor, the following effects have e.g. been reported:

Antidepressive effect, improvement of the sleep quality (Meert, T. F.; Janssen, P. A. J. Drug. Dev. Res. 1989, 18, 119.) and the negative symptoms of schizophrenia and reduction of extrapyramidal side-effects caused by treatment with classical neuroleptics in schizophrenic patients (Gelders, Y. G., British J. Psychiatry, 1989, 155 (suppl. 5, 33). Finally, selective 5-HT$_{2A}$ antagonists could be effective in the prophylaxis and treatment of migraine (Scrip Report; "Migraine—Current trends in research and treatment"; PJB Publications Ltd.; May 1991).

Clinical studies have shown that 5-HT$_{1A}$ partial agonists are useful in the treatment of anxiety disorders such as generalised anxiety disorder, panic disorder, and obsessive compulsive disorder (Glitz, D. A., Pohl, R., Drugs 1991, 41, 11). Preclinical studies indicate that also full agonists are useful in the treatment of the above mentioned anxiety related disorders (Schipper, Human Psychopharmacol., 1991, 6, 853).

There is also evidence, both clinical and preclinical, in support of the beneficial effect of 5-HT$_{1A}$ partial agonists in the treatment of depression, impulse control disorders and alcohol abuse (van Hest, Psychopharmacol., 1992, 107, 474; Schipper et al, Human Psychopharmacol., 1991, 6, S53; Cervo et al, Eur. J. Pharm., 1988, 158, 53; Glitz and Poh, Drugs 1991, 41, 11; Grofet al., Int. Clin. Psychopharmacol. 1993, 8, 167–172; Ansseau et al, Human Psychopharmacol. 1993, 8, 279–283).

5-HT$_{1A}$ agonists and partial agonists inhibit isolation induced aggression in male mice indicating that these compounds are useful in the treatment of aggression (Sanchez et al., Psychopharmacology, 1993, 110, 53–59).

Furthermore, 5-HT$_{1A}$ ligands have been reported to show antipsychotic effect in animal models (Wadenberg and Ahlenius, J. Neural. Transm., 1991t 83, 43; Ahlenius, Pharmacol. & Toxicol., 1989, 64, 3; Lowe et al., J. Med. Chem., 1991, 34, 1860; New et al., J. Med. Chem., 1989, 32, 1147; and Martin et al., J. Med. Chem., 1989, 32, 1052).

Recent studies also indicate that 5-HT$_{1A}$ receptors are important in the serotonergic modulation of haloperidol-induced catalepsy (Hicks, Life Science 1990, 47, 1609, Wadenberg et al. Pharmacol. Biochem. & Behav. 1994, 47, 509–513) suggesting that 5-HT$_{1A}$ agonists are useful in the treatment of EPS induced by conventional antipsychotic agents such as haloperidol.

5-HT$_{1A}$ agonists have shown neuroprotective properties in rodent models of focal and global cerebral ischaemia and may, therefore, be useful in the treatment of ischaemic disease states (Prehn, Eur. J. Pharm. 1991, 203, 213).

Pharmacological studies have been presented indicating that 5-HT$_{1A}$ antagonists are useful in the treatment of senile dementia (Bowen et al, Trends Neur. Sci. 1992, 15, 84).

5-HT reuptake inhibitors are well known antidepressant drugs.

Accordingly, dopamine $D_4$ receptor ligands are potential drugs for the treatment of psychosis and positive symptoms of schizophrenia and compounds with combined effects at dopamine $D_4$ and serotonergic receptors may have the further benefit of improved effects on other psychiatric symptoms in schizophrenic patients such as depressive and anxiety symptoms. As 5-HT$_{1A}$ and 5-HT$_{2A}$ receptor ligand classes of compounds and 5-HT reuptake inhibitors have different activities in different animal models predictive of anxiolytic and antiaggressive effects (Perregaard et al., Recent Developments in Anxiolytics. Current Opinion in Therapeutic Patents 1993, 1, 101–128) and/or in models predictive of effects in other psychic disorders it might also be highly beneficial to have such combined serotonergic effects.

SUMMARY OF THE INVENTION

The object of the invention is to provide compounds with dopamine $D_4$ activities or with combined effects at dopamine $D_4$ receptors and serotonergic receptors and/or the serotonergic transporter.

It has now been found that certain substituted indane or dihydroindole compounds have effects at dopamine $D_4$ receptors. Additionally, many of the compounds interact with central serotonergic receptors, in particular with the $5\text{-}HT_{1A}$ and/or the $5\text{-}HT_{2A}$ receptors and/or they act as 5-HT reuptake inhibitors.

Accordingly, the present invention relates to novel compounds of the formula I.

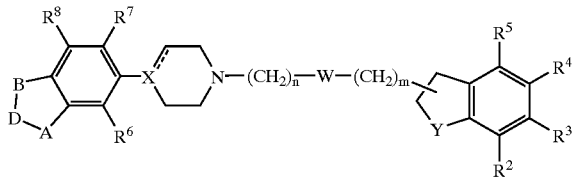

wherein A and B are independently O or S;

D is a methylene group optionally substituted with one or two $C_{1-4}$ alkyl groups;

Y is a hydrocarbon group completing an indane ring, a group $NR^1$ completing a dihydroindole ring, or a group N completing a dihydroindole ring attached via the 1-position;

W is a bond, and n+m is 1, 2, 3, 4, 5, or 6;

W is CO, SO, or $SO_2$, n is 2, 3, 4, or 5 and m is 0, 1, 2, or 3, provided that n+m is not more than 6; or W is O, S, n is 2, 3, 4, or 5 and m is 0, 1, 2, or 3, provided that n+m is not more than 6, and provided that when Y is N completing a dihydroindole ring attached via the 1-position then m is 2, or 3; and when Y is $NR^1$ completing a dihydroindole ring linked via the 2-position then m is 1, 2, or 3;

the dotted line, emanating from X, indicates an optional bond; when it does not indicate a bond X is N, CH or COH; and when it indicates a bond X is C;

$R^1$ is selected from
hydrogen, $C_{1-6}$ alkyl, $C_{2-6}$ alkenyl, $C_{2-6}$ alkynyl, $C_{3-8}$ cycloalk(en)yl, $C_{3-8}$ cycloalk(en)yl-$C_{1-6}$ alk(en/yn) yl, aryl, heteroaryl, aryl-$C_{1-6}$ alkyl, heteroaryl-$C_{1-6}$ alkyl, acyl, thioacyl, $C_{1-6}$ alkylsulfonyl, trifluoromethylsulfonyl, arylsulfonyl or heteroarylsulfonyl, or $R^{15}VCO$— wherein V is O or S and $R^{15}$ is $C_{1-6}$ alkyl, $C_{3-8}$ cycloalkyl, $C_{3-8}$ cycloalkyl-$C_{1-6}$ alkyl, aryl or heteroaryl, or a group $R^{16}R^{17}NCO$— or $R^{16}R^{17}NCS$— wherein $R^{16}$ and $R^{17}$ are independently hydrogen, $C_{1-6}$ alkyl, $C_{3-8}$ cycloalkyl, $C_{3-8}$ cycloalkyl-$C_{1-6}$ alkyl, aryl or heteroaryl, or $R^{16}$ and $R^{17}$ together with the N-atom to which they are linked, form a pyrrolidinyl, piperidinyl or perhydroazepin group;

$R^2$–$R^5$ are independently selected from hydrogen, halogen, cyano, nitro, $C_{1-6}$ alk(en/yn)yl, $C_{1-6}$ alkoxy, $C_{1-6}$ alkylthio, hydroxy, $C_{3-8}$ cycloalk(en)yl, $C_{3-8}$ cycloalk(en)yl-$C_{1-6}$ alk(en/yn)yl, $C_{1-6}$ alkylcarbonyl, phenylcarbonyl, halogen substituted phenylcarbonyl, trifluoromethyl, trifluoromethylsulfonyloxy and $C_{1-6}$ alkylsulfonyl, one of $R^2$–$R^5$ alternatively being a group —$NR^{13}R^{14}$ wherein $R^{13}$ is selected from the $R^1$ substituents; $R^{14}$ is hydrogen, $C_{1-6}$ alkyl, $C_{2-6}$, alkenyl, $C_{2-6}$, alkynyl, $C_{3-8}$ cycloalk (en)yl, $C_{3-8}$, cycloalk(en)yl-$C_{1-6}$ alk(en/yn)yl, aryl, heteroaryl, aryl-$C_{1-6}$ alkyl or heteroaryl-$C_{1-6}$ alkyl, or $R^{13}$ and $R^{14}$ together with the N-atom to which they are linked form a group

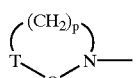

wherein Q is C=O, C=S or $CH_2$; T is NH, S, O or $CH_2$; and p is 1–4, wherein Q is C=O, C=S or $CH_2$; T is NH, S, O or $CH_2$; and p is 1–4, inclusive;

or two adjacent groups taken from $R^2$–$R^5$ may be joined and designate a —$(CH_2)_3$— or —CH=CH—NH— thereby forming a fused 5-membered ring;

$R^6$–$R^8$ are independently hydrogen, halogen, cyano, nitro, $C_{1-6}$-alk(en/yn)yl, $C_{1-6}$-alkoxy, $C_{1-6}$-alkylthio, hydroxy, trifluoromethyl, or $C_{1-6}$ alkylsulfonyl;

with the proviso that the substituent $R^3$ or $R^4$ in 6-position may not be —$NR^{13}R^{14}$ when Y is $CH_2$ and the ring is linked via the 1-position; and pharmaceutically acceptable acid addition salts thereof.

The compounds of the invention have been found to show high affinity for dopamine $D_4$ receptors and some of the compounds were found also to show affinity for serotonergic receptors including $5\text{-}HT_{1A}$ receptors and/or for $5\text{-}HT_{2A}$ receptors. In addition to the effects at these receptor subtypes, certain of the present compounds also show 5-HT reuptake inhibiting effect.

Accordingly, the compounds of the invention are considered useful in the treatment of positive and negative symptoms of schizophrenia, other psychoses, anxiety disorders, such as generalised anxiety disorder, panic disorder, and obsessive compulsive disorder, depression, alcohol abuse, impulse control disorders, aggression, side effects induced by conventional antipsychotic agents, ischaemic disease states, migraine, senile dementia and cardiovascular disorders and in the improvement of sleep.

In another aspect the invention provides a pharmaceutical composition comprising at least one compound of Formula I as defined above or a pharmaceutically acceptable acid addition salt thereof or prodrug thereof in a therapeutically effective amount and in combination with one or more pharmaceutically acceptable carriers or diluents.

In a further aspect the present invention provides the use of a compound of Formula I as defined above or an acid addition salt or prodrug thereof for the manufacture of a pharmaceutical preparation for the treatment of the above mentioned disorders.

DETAILED DESCRIPTION OF THE INVENTION

Some of the compounds of general Formula I exist as optical isomers thereof and such optical isomers are also embraced by the invention.

Prodrugs of the compounds of general Formula I are also embraced by the invention.

The expression $C_{1-6}$-alk(enlyn)yl means that the group may be an $C_{1-6}$-alkyl, $C_{2-6}$-alkenyl, or $C_{1-6}$-alkynyl group.

The expression $C_{3-8}$-cycloalk(en)yl means a $C_{3-8}$-cycloalkyl group, or a $C_{3-8}$-cycloalkenyl group.

The term $C_{1-6}$ alkyl refers to a branched or unbranched alkyl group having from one to six carbon atoms inclusive, such as methyl, ethyl, 1-propyl, 2-propyl, 1-butyl, 2-butyl, 2-methyl-2-propyl and 2-methyl-1-propyl.

Similarly, $C_{2-6}$ alkenyl and $C_{2-6}$ alkynyl, respectively, designate such groups having from two to six carbon atoms, inclusive. Preferred groups are those having from two to four carbon atoms.

The terms $C_{1-6}$ alkoxy, $C_{1-6}$ alkylthio, $C_{1-6}$ alkylsulfonyl, $C_{1-6}$ alkylamino, $C_{1-6}$ alkylcarbonyl, etc. designate such groups in which the alkyl group is $C_{1-6}$ alkyl as defined above.

The term $C_{3-8}$ cycloalkyl designates a monocyclic or bicyclic carbocycle having three to eight C-atoms, such as cyclopropyl, cyclopentyl, cyclohexyl, etc.

The term $C_{3-8}$ cycloalkenyl designates a monocyclic or bicyclic carbocycle having three to eight C-atoms and containing a double bond.

The term aryl refers to a mono- or bicyclic carbocyclic aromatic group, such as phenyl, and naphthyl, in particular phenyl.

The term heteroaryl refers to a mono- or bicyclic heterocyclic aromatic group, such as indolyl, thienyl, pyrimidyl, oxazolyl, isoxazolyl, thiazolyl, isothiazolyl, imidazolyl, benzofuranyl, benzothienyl, pyridyl, and furanyl, in particular pyrimidyl, indolyl, and thienyl.

Halogen means fluoro, chloro, bromo or iodo.

As used herein the term acyl refers to a formyl, $C_{1-6}$ alk(en/yn)ylcarbonyl, arylcarbonyl, aryl-$C_{1-6}$ alk(en/yn)ylcarbonyl, cycloalkylcarbonyl, or cycloalkyl-$C_{1-6}$ alk(en/yn)ylcarbonyl group and the term thioacyl is the corresponding acyl group in which the carbonyl group is replaced with a thiocarbonyl group.

The expression alk(en/yn)yl means that the group may be an alkyl, alkenyl, or alkynyl group.

As indicated in Formula I, the Y comprising ring may have a variable attachment point. Thus it may be linked to the W—(CH$_2$)$_n$ group via the 1- or 2-position when Y is hydrocarbon or the 1-, 2- or 3-position when Y is NR$^1$.

In Formula I, X is preferably —C= or —CH— and Y is preferably hydrocarbon or NR$^1$ wherein R$^1$ is hydrogen, $C_{1-6}$ alkyl, or $C_{1-6}$ alkylcarbonyl. Most preferably Y is CH$_2$ and in that case the indane ring is preferably linked via the 1-position.

W is preferably a bond and n+m is preferably 1–4, in particular 1 or 2.

R$^1$ is preferably hydrogen, methyl or acetyl most preferably hydrogen.

Each of R$^2$–R$^5$ is preferably hydrogen, halogen, cyano or one of them a group NR$^{13}$R$^{14}$ wherein R$^{13}$ is acyl, $C_{1-6}$ alkyl, $C_{1-6}$ alkoxy or a group R$^{16}$R$^{17}$NCO wherein R$^{16}$ is hydrogen, $C_{1-6}$ alkyl, $C_{3-8}$ cycloalkyl, cycloalkyl-$C_{1-6}$ alkyl, aryl or heteroaryl and R$^{17}$ is hydrogen or lower alkyl or R$^{16}$ and R$^{17}$ together with the N-atom to which they are linked, form a pyrrolidinyl, piperidinyl or perhydroazepin group. More preferably, R$^{13}$ is formyl, acetyl, methylaminocarbonyl, methylaminothiocarbonyl, dimethylaminocarbonyl, dimethylaminothiocarbonyl, methylsulfonyl, aminocarbonyl, cyclo propylcarbonyl, methyl, pyrrolidinylcarbonyl or 4-fluorophenylaminocarbonyl and R$^{14}$ is preferably hydrogen or lower alkyl, most preferably hydrogen or methyl, or R$^{13}$ and R$^{14}$ are linked together to form a 5–7 membered unsubstituted lactam ring or a pyrrolidinyl, piperidinyl or perhydroazepin.

R$^6$ to R$^8$ are preferably selected from hydrogen, halogen, cyano, nitro, $C_{1-6}$-alk(en/yn)yl, $C_{1-6}$-alkoxy, $C_{1-6}$-alkylthio, hydroxy, trifluoromethyl, or $C_{1-6}$ alkylsulfonyl. More preferred R$^6$ to R$^8$ are selected from hydrogen, halogen, $C_{1-6}$-alkyl, $C_{1-6}$-alkoxy.

A and B are preferably both O.

D is preferably methylene or methylene substituted with methyl, dimethyl formyl or acetyl.

A preferred subclass of compounds are those wherein Y is CH$_2$ the resulting indane ring being linked via the 2-position, A and B are both O and D is optionally substituted methylene.

In another subclass of compounds Y is CH$_2$ the resulting indane ring being linked via the 1-position, A and B are both O and D is optionally substituted methylene.

In another subclass of compounds Y is NR$^1$ the dihydroindole ring being linked via the 3-or 1-position, preferably the 3-position, A and B are both O and D is optionally substituted methylene.

In a further subclass of compounds are those wherein W is a bond.

Another subclass of compounds of the invention are those wherein one of R$^2$–R$^5$ is a group —NR$^{13}$R$^{14}$.

In yet another subclass of compounds of the invention neither of R$^2$–R$^5$ is a group —NR$^{13}$R$^{14}$.

In yet another subclass of compounds of the invention X is N.

In a last subgroup of compounds of the invention at least one of A and B is S.

The acid addition salts of the invention are pharmaceutically acceptable salts of the compounds of Formula I formed with non-toxic acids. Exemplary of such organic salts are those with maleic, fumaric, benzoic, ascorbic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzenesulfonic, and theophylline acetic acids, as well as the 8-halotheophyllines, for example 8-bromotheophylline. Exemplary of such inorganic salts are those with hydrochloric, hydrobromic, sulfuric, sulfamic, phosphoric, and nitric acids. The pharmaceutical compositions of this invention or those which are manufactured in accordance with this invention may be administered by any suitable route, for example orally in the form of tablets, capsules, powders, syrups, etc., or parenterally in the form of solutions for injection. For preparing such compositions, methods well known in the art may be used, and any pharmaceutically acceptable carriers, diluents, excipients, or other additives normally used in the art may be used.

Conveniently, the compounds of the invention are administered in unit dosage form containing said compounds in an amount of about 0.01 to 100 mg. The total daily dose is usually in the range of about 0.05–500 mg, and most preferably about 0.1 to 50 mg of the active compound of the invention.

The compounds of the invention may be prepared as follows:

a) alkylating a piperazine, piperidine, or tetrahydropyridine of the formula II with an alkylating derivative of the formula III:

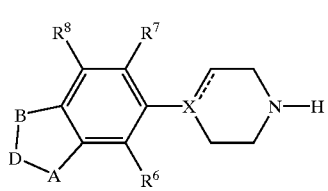

II

III

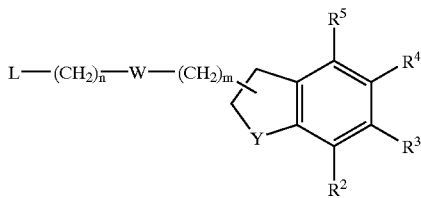

wherein $R^2$–$R^8$, X, Y, A, B, D, n, m, W, and the dotted line are as previously defined, and L is a leaving group such as eg. halogen, mesylate, or tosylate; or b) reducing the amide carbonyl in a compound of the following Formula IV:

IV

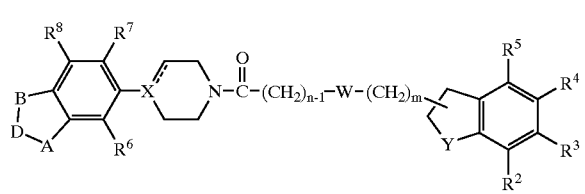

wherein $R^2R^8$, X, Y, A, B, D, m, W and the dotted line are as previously defined and n is 1, 2, 3, 4 or 5; or c) introducing a substituent $R^{2'}$, $R^{3'}$, $R^{4'}$ or $R^{5'}$ by reacting a compound of the following Formula V:

V

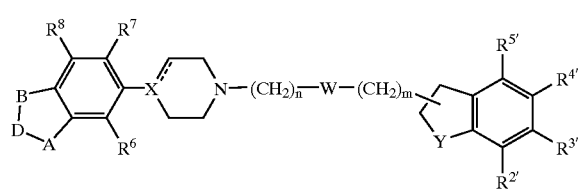

wherein one of $R^{2'}$–$R^{5'}$ is hydrogen and the others are the corresponding $R^2$, $R^3$, $R^4$, or $R^5$ as previously defined and $R^6$–$R^8$, X, Y, A, B, D, m, n, W, and the dotted line are as previously defined, by using a reactive reagent such as a halogen or a halogenating agent, a sulfonating agent, a nitration agent or a reactive agent generating carbonium ions ($RCO^+$, $R^+$) wherein R is alkyl alkynyl, aryl cycloalkyl, heteroaryl cycloalkyl, or cycloalk(en/yn)yl; or d) reducing the double bond in an indole compound of the following Formula VI:

VI

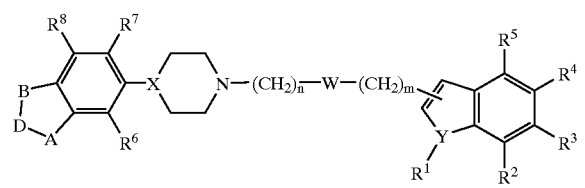

wherein $R^1$, $R^2$–$R^8$, A, B, C, X, n, m and W are as previously defined; or e) reducing the tetrahydropyridinyl double bond in derivatives of the following Formula VII:

VII

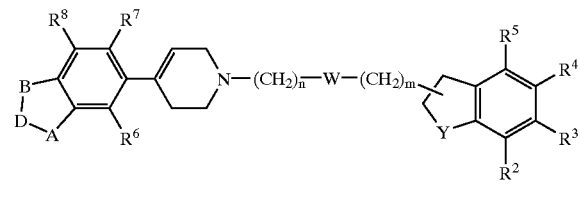

wherein $R^2$–$R^8$, Y, n, m, W, A, B and D are as previously defined; or f) Reacting a dihydroindole derivative of formula VIII:

VIII

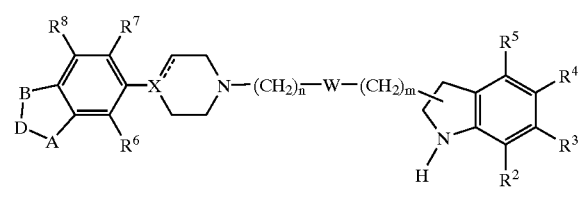

wherein $R^2$–$R^8$, X, A, B, D, n, m, W, and the dotted line are as previously defined, with a reagent of the formula $R^1$—L, where L is a leaving group such as halogen, mesylate or tosylate and $R^1$ is as previously defined, or of the formula $R^{1'}$-hal or $R^{1'}$—OCOR, in which formulas hal is halogen, $R^{1'}$ is acyl, thioacyl, a group $R^{15}VCO$—, or a group $R^{16}R^{17}NCO$— or $R^{16}R^{17}NCS$— where $R^{15}$, V, $R^{16}$ and $R^{17}$ are as previously defined except that neither $R^{16}$ nor $R^{17}$ may be hydrogen, or with a lower alkylsulfonyl halogenide, trifluoromethylsulhonyl halogenide or an isocyanate or thio-isocyanate of the formula $R^{16}$—N=C=O or $R^{16}$—N=C=S wherein $R^{16}$ is as previously defined;

g) reacting an anilino derivative of the formula IX:

IX

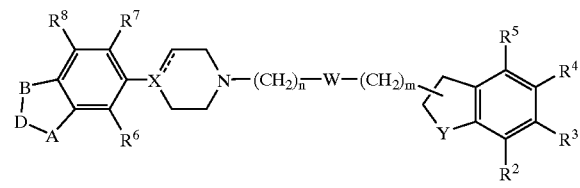

wherein one of $R^2$–$R^5$ is $NHR^{14}$, and $R^{14}$ is defined as above and the other $R^2$–$R^8$, X, Y, A, B, D, n, m, W, and the dotted line are as previously defined, with a reagent of the formula $R^{13}$—L, where L is a leaving group such as halogen, mesylate or tosylate and $R^{13}$ is as previously defined, or of the formula $R^{13'}$-hal or $R^{13'}$—OCOR, in which formulas hal is halogen, $R^{13'}$ is acyl, thioacyl, a group $R^{15}VCO$—, or a group $R^{16}R^{17}NCO$— or $R^{16}R^{17}NCS$— where $R^{15}$, V, $R^{16}$ and $R^{17}$ are as previously defined except that neither $R^{16}$ nor $R^{17}$ may be hydrogen, or with a lower alkylsulfonyl halogenide, trifluoromethylsulhonyl halogenide or an isocyanate or thioisocyanate of the formula $R^{16}$—N=C=O or $R^{16}$—N=C=S wherein $R^{16}$ is as previously defined, h) Alkylating a dihydroindole derivative of the Formula X with an alkylating derivative of the Formula XI:

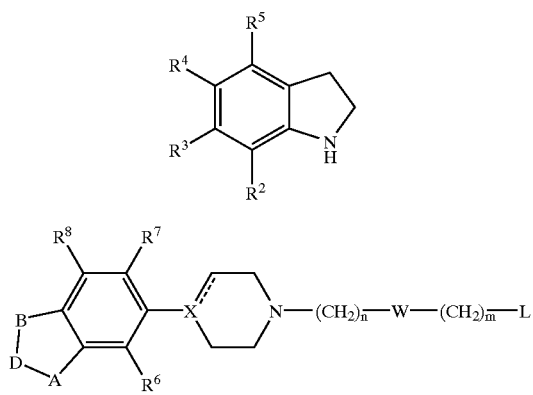

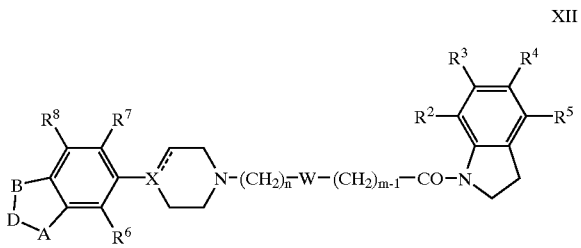

wherein $R^2$–$R^8$, X, Y, A, n, m, W, and the dotted line are as previously defined, and L is a leaving group such as eg. halogen, mesylate, or tosylate; or i) reducing the carbonyl amide compounds of Formula XII:

wherein $R^2$–$R^8$, X, Y, A, n, W and the dotted line are as previously defined and m is 1, 2, 3, 4 or 5; whereupon the compound of Formula I is isolated as the free base or a pharmaceutically acceptable acid addition salt thereof.

The reaction in Methods f) and g) are conveniently performed at low temperature (eg. below room temperature) in an inert solvent such as acetone, dichloromethane, tetrahydrofuran or dimethoxyethane when reactive carboxylic acid chlorides, isocyanates, or isothiocyanates are used. Formylated amines are prepared from the corresponding amines by reaction in formic acid, with esters of formic acid, or by reaction with mixed formic acid anhydride prepared in situ. Generally reaction temperatures are between 0° C. and the boiling point of the formnyl precursor compounds.

The alkylations according to Methods a) and h) are generally performed by refluxing in a suitable solvent such as acetone, methyl isobutyl ketone, tetrahydrofuran, dioxane, ethanol or 2-propanol in the presence of a base such as triethylamine or potassium carbonate.

The reductions of double bonds according to Methods d) and e) are generally performed by catalytic hydrogenation at low pressure (<3 atm.) in a Parr apparatus, or by using reducing agents such as diborane or hydroboric derivatives as produced in situ from $NaBH_4$ in trifluoroacetic acid in inert solvents such as tetrahydrofuran, dioxane, or diethyl ether.

The reductions according to Method b) and i) are generally performed by use of $LiAlH_4$, $AlH_3$ or diborane in an inert solvent such as tetrahydrofuran, dioxane, or diethyl ether at room temperature or at a slightly elevated temperature.

The halogenation according to Method c) is generally performed by use of chlorine, bromine, or N-chlorosuccinimide, N-bromosuccinimide or another halogen precursor molecule, conveniently in the presence of a catalyst such as Fe ions or a mineral acid.

Methylene- or ethylenedioxyphenylpiperazine, piperidine and tetrahydropyridyl starting materials are commercially available or may be prepared by literature procedures.

Key intermediates such as 1-indanecarboxylic acid (V. Asham and W. H. Linnell, *J. Chem. Soc.* 1954, 4691–4693, Hansen et al. *Helv. Chim. Acta* 1982, 33, 325–343) and 6-nitro-1-indanecarboxylic acid (G. Kirsch et al. *Just. Lieb. Ann. Chem.* 1976, 10, 1914) were prepared according to well-known literature procedures.

EXPERIMENTAL SECTION

Melting points were determined on a Büichi SMP-20 apparatus and are uncorrected. Mass spectra were obtained on a Quattro MS-MS system from VG Biotech, Fisons Instruments. The MS-MS system was connected to an HP 1050 modular HPLC system. A volume of 20–50 $\mu$l of the sample (10 $\mu$g/ml) dissolved in a mixture of 1% acetic acid in acetonitril/water 1:1 was introduced via the autosampler at a flow of 30 $\mu$l/min into the Electrospray Source. Spectra were obtained at two standard sets of operating conditions. One set to obtain molecular weight information (MH+) (21 eV) and the other set to induce fragmentation patterns (70 eV). The background was subtracted. The relative intensities of the ions are obtained from the fragmentation pattern. When no intensity is indicated for the Molecular Ion (MH+) this ion was only present under the first set of operating conditions. 1H NMR spectra were recorded of all novel compounds at 250 MHz on a Bruker AC 250. Deuterated chloroform (99.8%D) or dimethylsulfoxide (99.9%D) were used as solvents. TMS was used as internal reference standard. Chemical shift values are expressed in ppm-values. The following abbreviations are used for multiplicity of NMR signals: s=singlet, d=doublet, t=tiplet, q=quartet, qui=quintet, h=heptet, dd=double doublet, dt=double triplet, dq=double quartet, tt=triplet of triplets, m=multiplet. NMR signals corresponding to acidic protons are generally omitted. Content of water in crystalline compounds was determined by Karl Fischer titration. Standard workup procedures refer to extraction with the indicated organic solvent from proper aqueous solutions, drying of combined organic extracts (anhydrous $MgSO_4$ or $Na_2SO_4$), filtering and evaporation of the solvent in vacuo. For column chromatography silica gel of type Kieselgel 60, 230–400 mesh ASTM was used.

EXAMPLE 1

1-Indanylmethanol, 1a

To a suspension of $LiAlH_4$ (4.7 g) in diethyl ether (200 ml) was added dropwise a solution of $AlCl_3$ in diethyl ether (200 ml). A solution of 1-indanecarboxylic acid (10 g) (prepared according to the method of Hansen et al. *Helv. Chim. Acta* 1982, 33, 325–343) in dry tetrahydrofuran (200 ml) was added dropwise at 10–15° C. The mixture was finally stirred at room temperature for 1.5 hours. Excess $AlH_3$ was destroyed by addition of concentrated aqueous NaOH solution (25 ml) at 0° C. Precipitated inorganic salts were filtered off and the solvents evaporated in vacuo leaving 6.8 g of the title compound 1a as a viscous oil which was used without further purification.

The following -indanylmethanols were prepared in a similar manner: 6-Bromo-1-indanylmethanol from alane reduction of the corresponding methyl 6-bromo-1-indanecarboxylic acid ester, isolated as a viscous oil. 1b.

EXAMPLE 2

6-Cyano-1-indanylmethanol 2a

To a solution of 6-bromo-1-indanylmethanol (20 g) in N-methyl-2-pyrrolidone (NMP) (380 ml) was added CuCN (79 g). The mixture was heated at 160° C. for 6 hours. After cooling to 80–90° C. the mixture was poured into an aqueous solution (500 ml) of NaCN (4g). After stirring for 20 minutes excess CuCN was filtered off. Ethyl acetate (300 ml) was added and the organic phase was separated and worked-up. The remaining oil was dissolved in diethyl ether (300 ml) and washed with saturated brine (2×100 ml). The organic phase was separated and worked up according to the general procedure leaving 14.6 g of crude title compound 2a as a viscous oil. Column chromatography on silica gel (eluent:ethylacetat/heptane 6:4) afforded pure 2a (8.7 g) which was used without further purification.

EXAMPLE 3

6-Cyano-1-indanylmethanol Methanesulfonate, 3a

To a solution of 6-cyano-1-indanylmethanol 2a (3 g) and triethylamine (2.8 ml) in dichloromethane (50 ml) was added dropwise a solution of methansulfonylchloride (1.5 ml) in dichloromethane (25 ml) at 0° C. The mixture was stirred at room temperature for 1 hour. Water was added (200 ml) and the organic phase was subsequently separated and worked-up according to the standard procedure above. The remaining crystalline product was stirred with diethyl ether and filtered off. Yield 2.7 g. Mp 62–63° C.

The following methanesulfonates were prepared in a similar manner: 1-Indanylmethanol methanesulfonate, 3b. Isolated as a viscous oil 6-Bromo-1-indanylmethanol methanesulfonate, 3c.

EXAMPLE 4

Method a 1-(1-Indanylmethyl-4-(3,4-methylenedioxyphenyl)piperazine, Fumarate, 4a A mixture of 1-Indanylmethanol methanesulfonate, 3b (5.8 g) and 1-(3,4-methylene-dioxyphenyl)piperazine (commercially available) (11 g) in NMP (100 ml) was heated at 110° C. for 5 hours. After cooling to room temperature the mixture was poured into diluted aqueous $NH_4OH$. Extraction with a 1:1 mixture of diethyl ether/ethyl acetate (3×100 ml) afforded 13.1 g of a very impure product. Purification by column chromatography on silica gel (eluted with heptane/ethyl acetate/triethylamine 80/20/4) yielded pure title compound (2.7) which precipitated as the fuimarate salt 4a from ethanol. Mp>311° C. $^1H$ NMR (DMSO-$d_6$): d 1.70–1.90 (m, 1H); 2.15–2.30 (m, 1H); 2.45 (dd, 1H); 2.65 (broad t, 4H); 2.55–2.70 (m, 2H); 2.70–2.95 (m, 2H); 3.05 (broad t, 4H); 3.35 (quin, 1H); 5.85 (s, 2H); 6.45 (dd, 1H); 6.65 (s, 2H); 6.70 (d, 1H); 6.75 (d, 1H); 7.15–7.30 (m, 3H); 7.35 (dd, 1H); MS m/z (%): 337 (MH+, 62%), 207 (24%), 131 (100%).

In a similar way the following compound was prepared:

1-(6-Bromo-1-indanylmethyl-4-(3,4-methylenedioxyphenyl)piperazine, Fumarate, 4b mp 158–161° C. $^1H$ NMR (DMSO-$d_6$): d 1.65–1.80 (m, 1H); 2.10–2.25 (m, 1H); 2.40 (dd, 1H); 2.60 (broad t, 4H); 2.50–2.60 (m, 2H); 2.65–2.90 (m, 2H); 3.05 (broad t, 4H); 3.40 (quin, 1H); 5.95 (s, 2H); 6.35 (dd, 1H); 6.65 (s, 2H); 6.70 (d, 1H); 6.75 (d, 1H); 7.15 (d, 1H); 7.25 (dd, 1H); 7.55 (d,1H). MS m/z (%): 417 (35%), 415 (MH+, 35%), 219 (30%), 209 (32%), 206 (30%), 164 (24%), 130 (100%).

EXAMPLE 5

1-[2-[4-(3,4-Methylenedioxyphenyl)-piperazine-1-yl]methylearbonyl]-indane, 5a A solution of indane-1-acetic acid (Anderson, A. G. et al; J. Org. Chem. 1973, 38(8), 1439–1444) (2.5 g, 14.2 mmol), DMF (1 ml) and $SOCl_2$ (6.2 g, 52.5 mmol) in $CH_2Cl_2$ (100 ml) was refluxed for 4 h. The mixture was evaporated and re-evaporated from toluene to give the corresponding acid chloride. To a solution of 1-(3,4-methylenedioxyphenyl)-piperazine hydrochloride (6.9 g, 28.4 mmol) and TEA (6 ml) in TBE (70 ml) was added dropwise over 20 min. a solution of the acid chloride in THE (70 ml). The mixture was stirred for 1 h and evaporated. $H_2O$ (30 ml) was added to the remanence and the mixture was extracted with $CH_2Cl_2$ (2×100 ml). After washing with $H_2O$ (10 ml) and brine (10 ml) the combined organic phases were dried with $MgSO_4$ and evaporated. The product was purified by column chromatography (EtOAc:heptane=1:1) to give the title compound 5a (3.3 g, 64%): 1H NMR (DMSO-$d_6$) d 1.65–1.82 (1H, m), 2.34–2.54 (2H, m), 2.72–2.83 (1H, dd), 2.86–3.07 (6H, m), 3.48–3.59 (2H, m), 3.62–3.76 (1H, m), 3.77–3.82 (2H, m), 5.88 (2H, s), 6.32 (1H, dd), 6.53 (1H, d), 6.70 (1H, d), 7.11–7.25 (4H, m).

The following amide was prepared in a similar manner: 2-[4-(3,4-Methylenedioxyphenyl)-piperazine-1-yl] carbonyl]-indane, 5b mp 114–116° C.

This compound was prepared from indane-2-carboxylic acid which again was prepared by heating a solution of indane-2,2-dicarboxylic acid (17 g, Baeyer and Perkin, Ber. 1884, 17, 122) in NMP (200 ml) to 150° C. for 1 hour. After cooling to 20° C. the solution was poured in water (300 ml) and concentrated hydrochloric acid was added to pH=1. Conventional work up with ether gave indane-2-carboxylic (4.7 g). Mp 132–33° C. (from ether).

EXAMPLE 6

1-[2-[4-(3,4-Methylenedioxyphenyl)-piperazine-1-yl]ethyl]-indane Fumarate, 6a To a supension of $LiAlH_4$ (1.0 g, 27.2 mmol) in THF (70 ml) was added dropwise over 20 min. a solution of 5a (3.3 g, 9.1 mmol) in THF (70 ml). The mixture was refluxed for 1.5 h and then cooled to 10–15° C. After dropwise addition of $H_2O$ (1 ml), aqueous (15%) NaOH (1 ml) and $H_2O$ (5 ml), the solution was filtered and evaporated to allmost dryness. The remanence was dissolved in $CH_2Cl_2$ and after drying with $MgSO_4$, the solution was evaporated to give the free base of 6a, which was dissolved in acetone (15 ml) and treated with fumaric acid (1.1 g) dissolved in EtOH to give the title compound 6a (2.5 g, 59%): mp 191–192° C., $^1H$ NMR (DMSO-$d_6$) d 1.45–1.70 (2H, m), 2.00–2.15 (1H, m), 2.15–2.30 (1H, m), 2.50–2.60 (2H, m), 2.65–2.70 (4H, m), 2.70–2.90 (2H, m), 3.00–3.20 (5H, m), 5.90 (1H, s), 6.30 (2H, dd), 6.60 (2H, s), 6.65 (1H, d), 6.70 (1H, d), 7.10–7.30 (4H, m). MS m/z (%): 351 (MH+, 100%), 188 (27%), 117 (19%).

The following compound was prepared in a similar way using compound 5b as starting material:

2-[4-(3,4-Methylenedioxyphenyl)-piperazine-1-yl] methyl]-indane, Oxalate, 6b mp 197–199° C. $^1H$ NMR (DMSO-$d_6$) d 2.70 (dd, 2H), 2.85 (quintet, 1H), 2.95–3.35 (m, 12H), 5.95 (s, 2H), 6.40 (dd, 1H), 6.75 (d, 1H), 6.80 (d, 1H), 7.10–7.25 (m, 4H). MS m/z (%): 337 (MH+, 100%), 174, (14%), 131(26%).

EXAMPLE 7

1-Acetyl-2,3-dihydro-3-[1-(2-methanesulphonyl) ethyl]-1H-indole, 7a

To a solution of indole-3-acetic acid (100 g) in methanol (1 l) was added ether saturated with HCl (200 ml), and the solution was left at room temperature for 3 hours. The solution as evaporated in vacuo, and the residue was dissolved in THF 1.2 l) and added slowly with cooling to a stirred suspension of $LiAlH_4$ (28.6 g) in THF (1 l). After stirring for 2 hours at room temperature, the mixture was cooled in an ice bath, and water (57 ml), 15% NaOH (29 ml), and water (143 ml) was added. The mixture was filtered and evaporated in vacuo, and the residue (84.9 g) was dissolved in dioxane (1.5 l). Borane trimethylamine complex (200 g) was added, and and to the stirred mixture was added concentrated hydrochloric acid (150 ml) during 1 hour. The mixture was heated to 40° C. for 30 minutes and then to reflux for 2.5 hours. Then 6 M hydrochloric acid (460 ml) was added and reflux was continued for 30 minutes. The solution was concentrated in vacuo, and the residue was poured on ice. The solution was washed with ether and was made basic with concentrated NaOH and then extracted with ether. The organic phase was dried over $MgSO_4$ and was evaporated in vacua. The residue was dissolved in $CH_2Cl_2$ (680 ml) and triethylamine (68 ml). Acetyl chloride (36 ml) was added at 5° C. during 1 hour. After further stirring for 1 hour at room temperature, the mixture was washed with dilute hydrochloric acid, and $NaHCO_3$ solution. After drying over $MgSO_4$ and evaporation in vacuo, the residue was dissolved in methanol (500 ml), and 30% Na-methanolat (10 ml) was added. The mixture was stirred for 4 hours at room temperature and was then evaporated in vacuo and was dissolved in $CH_2Cl_2$ and was washed with saturated NaCl solution, dried over $MgSO_4$ and evaporation in vacuo. The residue (75.4 g) was dissolved in $CH_2Cl_2$ (1 l) and triethylamine (100 ml). With cooling was added a solution of methanesulphonic chloride (27 ml) in $CH_2Cl_2$ (175 ml) at 10° C. After stirring for 30 minutes at 0° C. and 1 hour at room temperature, the mixture was evaporated in vacuo and was purified on silica gel eluted with ethyl acetate to give the title produduct as an oil (74 g).

EXAMPLE 8

1-(4-Chloro-1-oxobtutan-1-yl)-2,3-dihydro-1H-indole, 8a

The title compound was prepared in a similar way as Example 7 using a cooled solution of 2,3-dihydro-1H-indole (10 g) in $CH_2Cl_2$ (125 ml) and triethylamine (13 ml) by adding 4-chlorobutyryl chloride (10 ml) at less than 10° C. Conventional work up gave the title compound as an oil. Yield 16.4 g.

EXAMPLE 9

2,3-Dihydro-3-[4-[4[(3,4-methylenedioxyphenyl) piperazine-1-yl]butyl-1-oxo]]-1H-indole, Oxalate 9a A mixture of 3,4-methylenedioxyphenylpiperazine (2.50 g), 8a (2.78 g), and $K_2CO_3$ (1.85 g) in MIBK (100 ml) was heated to reflux for 16 hours. The mixture was filtrated and evaporated in vacuo, and the residue was dissolved in ethyl acetate and worked up in a conventional manner to give a crude product (3.5 g) which was purified on silica gel eluted with ethyl acetate-heptane triethylamine (64:31:5). The title oxalate was crystallized from acetone. Yield 0.20 g, mp 198–200° C. $^1$H NMR (DMSO-$d_6$) d 1.85–2.00 (m, 2H), 2.55 (t, 2H), 3.00 (t, 2H), 3.05–3.30 (m, 8H), 3.50–4.00 (m, 2H), 4.05 (t, 1H), 5.9 (s, 2H), 6.40 (dd, 1H), 6.75 (d, 1H), 6.80 (d, 1H), 7.00 (t, 1H), 7.15 (t, 1H), 7.25 (d, 1H), 8.10 (d, 1H).

1-Acetyl-2,3-dihydro-3-[2-[4-[(3,4-methylenedioxyphenyl)piperazine-1-yl]ethyl]]1H-indole, 9b From 7a and 3,4-methylenedioxyphenylpiperazine. Mp 185–7° C. 1H NMR (DMSO-d6) d 1.75–2.00 (m, 1H), 2.10–2.25 (m, 1H), 2.15 (s, 3H), 2.90–3.15 (m, 2H), 3.2 (d, 8H), 3.35–3.55 (m, 1H), 3.80 (dd, 1H), 4.20 (t, 1H), 5.90 (s, 2H), 6.35 (dd, 1H), 6.75 (d, 1H), 6.80 (d, 1H), 7.00 (t, 1H), 7.20 (t, 1H), 7.30 (d, 1H), 8.05 (d, 1H). MS m/z (%): 394 (MH+, 100%), 219 (3%), 146 (2%).

Pharmacological Testing

The compounds of the invention were tested in well recognized and reliable methods. The tests were as follows:

$^3$H-YM-09151-2 BINDING

By this method the inhibition by drugs of the binding of the dopamine $D_4$ antagonist $^3$H-YM-09151-2 to dopamine $D_4$ receptors in cloned human dopamine receptor subtype 4.2 membranes is determined in vitro. Accordingly, this is a test for affinity for dopamine $D_4$ receptors. The test is performed using a preparation of cloned dopamine $D_4$ cell membranes CRM-016®, Dupharma A/S, Denmark, in accordance with the product specifications. The results are given in the following Table 1 as $IC_{50}$-values.

TABLE 1

| Binding Data ($IC_{50}$ values in nM or % inhibition of binding at 50 nM) | |
|---|---|
| Comp. No | Binding |
| 4a | 8.8 |
| 4b | 33% at 50 nM |
| 6a | 5.6 |
| 6b | 1.8 |
| 9a | 4.3 |
| 9b | 3.7 |

$^3$H-8-OH-DPAT Binding.

By this method the inhibition by drugs of the binding of the 5-$HT_{1A}$ agonist $^3$H-8-OH-DPAT (1 nM) to 5-$HT_{1A}$ receptors in membranes from rat brain minus cerebellum is determined in vitro. Accordingly, this is a test for affinity for 5-$HT_{1A}$ receptor. The test is performed as described by Hyttel et al., Drug. Dev. Res., 1988, 15, 389–404.

$^3$H-Ketanserin Binding.

By this method the inhibition by drugs of the binding of $^3$H-Ketanserin (0,5 nM) to 5-$HT_{2A}$ receptors in membranes from rat is determined in vitro. The method is described in Hyttel, Pharmacology & Toxicology, 61, 126–129, 1987.

In addition to the above tests, the compounds of the invention were tested with respect to affinity for the dopamine $D_2$ receptor by determining their ability to inhibit the binding of $^3$H-spiroperidol to $D_2$ receptors by the method of Hyttel et al, J. Neurochem., 1985, 44, 1615. Furthermore, they were tested with respect to their 5-HT reuptake inhibiting effect by measuring their ability to inhibit the uptake of $^3$H-serotonin in rat brain synapsomes in vitro by the method descibed by Hyttel and Larsen, Acta Pharmacol. Tox., 1985, 56, suppl. 1, 146–153.

In general, the compounds of the invention have been found potently to inhibit the binding of tritiated YM-09151-2 to dopamine $D_4$ receptors. Furthermore, many of the compounds have been found to inhibit the binding of tritiated 8-hydroxy-2-dipropylaminotetralin (8-OH-DPAT) to $5\text{-HT}_{1A}$ receptors and/or the binding of $^3\text{H}$ ketanserin to $5\text{-HT}_2\text{A}$ receptors in vitro. Some compounds only bind to one of the two serotonin receptor subtypes, $5\text{-HT}_{1A}$ or $5\text{-HT}_{2A}$. In addition to these affects, a number of the compounds have proven to have the further advantage of a potent 5-HT reuptake inhibiting effect and/or effects at other serotonergic receptors. The compounds have no substantial or only weak affinity for the dopamine $D_2$ receptor.

Accordingly, the compounds of the invention are considered useful in the treatment of positive and negative symptoms of schizophrenia, other psychoses, anxiety disorders, such as generalised anxiety disorder, panic disorder, and obsessive compulsive disorder, depression, alcohol abuse, impulse control disorders aggression, side effects induced by conventional antipsychotic agents, ischaemic disease states, migraine, senile dementia and cardiovascular disorders and in the improvement of sleep.

FORMULATION EXAMPLES

The pharmaceutical formulations of the invention may be prepared by conventional methods in the art.

For example: Tablets may be prepared by mixing the active ingredient with ordinary adjuvants and/or diluents and subsequently compressing the mixture in a conventional tabletting machine. Examples of adjuvants or diluents comprise: corn starch, potato starch, talcum, magnesium stearate, gelatine, lactose, gums, and the like. Any other adjuvants or additives usually used for such purposes such as colourings, flavourings, preservatives etc. may be used provided that they are compatible with the active ingredients. Solutions for injections may be prepared by dissolving the active ingredient and possible additives in a part of the solvent for injection, preferably sterile water, adjusting the solution to desired volume, sterilisation of the solution and filling in suitable ampules or vials. Any suitable additive conventionally used in the art may be added, such as tonicity agents, preservatives, antioxidants, etc.

Typical examples of recipes for the formulation of the invention are as follows:

1) Tablets containing 5.0 mg of Compound 4a calculated as the free base:

| | |
|---|---|
| Compound 4a | 5.0 mg |
| Lactose | 60 mg |
| Maize starch | 30 mg |
| Hydroxypropylcellulose | 2.4 mg |
| Microcrystalline cellulose | 19.2 mg |
| Croscarmellose Sodium Type A | 2.4 mg |
| Magnesium stearate | 0.84 mg |

2) Tablets containing 0.5 mg of Compound 6a calculated as the free base:

| | |
|---|---|
| Compound 6a | 0.5 mg |
| Lactose | 46.9 mg |
| Maize starch | 23.5 mg |
| Povidone | 1.8 mg |
| Microcrystalline cellulose | 14.4 mg |
| Croscarmellose Sodium Type A | 1.8 mg |
| Magnesium stearate | 0.63 mg |

3) Syrup containing per millilitre:

| | |
|---|---|
| Compound 9b | 25 mg |
| Sorbitol | 500 mg |
| Hydroxypropylcellulose | 15 mg |
| Glycerol | 50 mg |
| Methyl-paraben | 1 mg |
| Propyl-paraben | 0.1 mg |
| Ethanol | 0.005 ml |
| Flavour | 0.05 mg |
| Saccharin natrium | 0.5 mg |
| Water | ad 1 ml |

4) Solution for injection containing per millilitre:

| | |
|---|---|
| Compound 4a | 0.5 mg |
| Sorbitol | 5.1 mg |
| Acetic Acid | 0.05 mg |
| Saccharin sodium | 0.5 mg |
| Water | ad 1 ml |

What is claimed is:
1. A dihydroindole compound of formula I

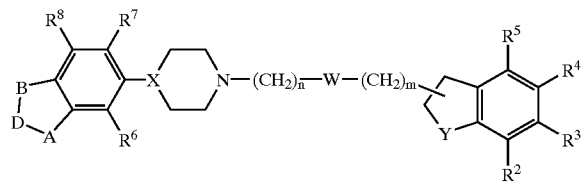

wherein A and B are independently O or S;
D is a methylene group optionally substituted with one or two $C_{1-4}$ alkyl groups;
Y is a group $NR^1$ completing a dihydroindole ring, or a group N completing a dihydroindole ring attached via the 1-position;
W is a bond, and n+m is 1, 2, 3, 4, 5, or 6;
W is CO, SO, or $SO_2$, n is 2, 3, 4, or 5 and m is 0, 1, 2, or 3, provided that n+m is not more than 6; or
W is O, S, n is 2, 3, 4, or 5 and m is 0, 1, 2, or 3, provided that n+m is not more than 6, and
provided that when Y is N completing a dihydroindole ring attached via the 1-position then m is 2 or 3; and when Y is $NR^1$ completing a dihydroindole ring linked via the 2-position then m is 1, 2, or 3;
$R^1$ is selected from
hydrogen, $C_{1-6}$ alkyl, $C_{2-6}$ alkenyl, $C_{2-6}$ alkynyl, $C_{3-8}$ cycloalk(en)yl, $C_{3-8}$ cycloalk(en)yl-$C_{1-6}$ alk(en/yn) yl, aryl, heteroaryl, aryl-$C_{1-6}$ alkyl, heteroaryl-$C_{1-6}$ alkyl, acyl, thioacyl, $C_{1-6}$ alkylsulfonyl, trifluoromethylsulfonyl, arylsulfonyl or heteroarylsulfonyl, or
$R^{15}VCO$— wherein V is O or S and $R^{15}$ is $C_{1-6}$ alkyl, $C_{3-8}$ cycloalkyl, $C_{3-8}$ cycloalkyl-$C_{1-6}$ alkyl, aryl or heteroaryl, or a group $R^{16}R^{17}NCO$— or $R^{16}R^{17}NCS$— wherein $R^{16}$ and $R^{17}$ are independently hydrogen, $C_{1-6}$ alkyl, $C_{3-8}$ cycloalkyl, $C_{3-8}$ cycloalkyl-$C_{1-6}$ alkyl, aryl or heteroaryl, or $R^{16}$ and $R^{17}$ together with the N-atom to which they are linked, form a pyrrolidinyl, piperidinyl or perhydroazepin group;
$R^2$–$R^5$ are independently selected from hydrogen, halogen, cyano, nitro, $C_{1-6}$ alk(en/yn)yl, $C_{1-6}$ alkoxy, $C_{1-6}$ alkylthio, hydroxy, $C_{3-8}$ cycloalk(en)yl, $C_{3-8}$ cycloalk(en)yl-$C_{1-6}$ alk(en/yn)yl, $C_{1-6}$ alkylcarbonyl, phenylcarbonyl, halogen substituted phenylcarbonyl, trifluoromethyl, trifluoromethylsulfonyloxy and $C_{16}$ alkylsulfonyl, one of $R^2$–$R^5$ alternatively being a group —$NR^{13}R^{14}$ wherein $R^{13}$ is selected from the $R^1$ substituents;

$R^{14}$ is hydrogen, $C_{1-6}$ alkyl, $C_{2-6}$ alkenyl, $C_{2-6}$ alkynyl, $C_{3-8}$ cycloalk(en)yl, $C_{3-8}$ cycloalk(en)yl-$C_{1-6}$alk(en/yn)yl, aryl, heteroaryl, aryl-$C_{1-6}$ alkyl or heteroaryl-$C_{1-6}$alkyl, or $R^{13}$ and $R^{14}$ together with the N-atom to which they are linked form a group

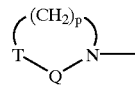

wherein Q is C=O, C=S or $CH_2$; T is NH, S, O or $CH_2$; and p is 1–4 inclusive;

$R^6$–$R^8$ are independently selected from hydrogen, halogen, cyano, nitro, $C_{1-6}$-alk(en/yn)yl, $C_{1-6}$-alkoxy, $C_{1-6}$-alkylthio, hydroxy, trifluoromethyl or $C_{1-6}$ alkylsulfonyl;

wherein any of the aryl groups or aryl moieties is selected from the group consisting of phenyl and napthyl, and any of the heteroaryl groups or heteroaryl moieties is selected from the group consisting of indolyl, thienyl, pyrimidyl, oxazolyl, isoxazolyl, thiazolyl, isothiazolyl, imidazolyl, benzofuranyl, benzothienyl, pyridyl and furanyl;

or a pharmaceutically acceptable acid addition salt thereof.

2. A compound of claim 1, wherein Y is $NR^1$ and the resulting dihydroindole ring is linked to the W—$(CH_2)_n$ group via the 1- or 3-position.

3. A compound of claim 2, wherein $R^1$ is hydrogen, $C_{1-6}$ alkyl, or $C_{1-6}$ alkylcarbonyl.

4. A compound of claim 1, wherein A and B are both O.

5. A compound of claim 1, wherein D is methylene or methylene substituted with one or two methyl groups.

6. A compound of claim 1, wherein W is a bond and n+m is 1, 2, 3 or 4.

7. A compound of claim 6, wherein n+m is 1 or 2.

8. A compound of claim 1, wherein none of $R^2$–$R^5$ is a group $NR^{13}R^{14}$.

9. A compound of claim 1, wherein each of $R^2$–$R^5$ is selected from the group consisting of hydrogen, halogen or cyano.

10. A compound of claim 1, wherein at least one of $R^2$–$R^5$ is a group $NR^{13}R^{14}$.

11. A compound of claim 1, wherein $R^{13}$ is acyl, $C_{1-6}$ alkyl $C_{1-6}$alkoxy or a group $R^{16}R^{17}NCO$— wherein $R^{16}$ is hydrogen, $C_{1-6}$ alkyl, $C_{3-8}$ cycloalkyl, cycloalkyl-$C_{1-6}$alkyl, aryl or heteroaryl and $R^{17}$ is hydrogen or $C_{1-6}$ alkyl, and $R^{14}$ is hydrogen or lower alkyl.

12. A compound of claim 11, wherein $R^{13}$ is formyl, acetyl, methylaminocarbonyl, methylaminothiocarbonyl, dimethylaminocarbonyl, dimethylaminothiocarbonyl, methylsulfonyl, aminocarbonyl, cyclopropylcarbonyl, methyl, pyrrolidinylcarbonyl or 4-fluorophenylaminocarbonyl.

13. A compound of claim 10, wherein $R^{13}$ and $R^{14}$ are linked together to form a 5–7 membered unsubstituted lactam ring or a pyrrolidinyl, piperidinyl or perhydroazepin group.

14. A compound of claim 2, wherein Y is $NR^1$, the dihydroindole ring is linked via the 3- or 2-position, A and B are both O, and D is optionally substituted methylene.

15. A compound of claim 14, wherein W is a bond.

16. A compound of claim 14, wherein n+m is 1 or 2, and $R^1$–$R^5$are all hydrogen.

17. A compound of claim 1, which is selected from the group consisting of:

2,3-Dihydro-3-[4-[4-[3,4-methylendioxyphenyl) piperazine-1-yl]butyl-1-oxo]]-1H-indole; or 1-Acetyl-2,3-dihydro-3[2-[4-[(3,4-methylendioxyphenyl) piperazine-1-yl]ethyl]]-1H-indole.

18. A method of treating positive and negative symptoms of schizophrenia and other psychoses, said method comprising administering a pharmaceutically effective amount of the compound of claim 1.

19. A pharmaceutical composition comprising a compound of claim 1 in a therapeutically effective amount together with one or more pharmaceutically acceptable carriers or diluents.

* * * * *

UNITED STATES PATENT AND TRADEMARK OFFICE
CERTIFICATE OF CORRECTION

PATENT NO. : 6,436,940 B2
DATED : August 20, 2002
INVENTOR(S) : Jens Kristian Perregaard, Ivan Mikkelsen and Henrik Pedersen It is certified that error appears in the above-identified patent and that said Letters Patent is hereby corrected as shown below:

Column 4,
Line 56, delete "(enlyn)" and replace with -- (en/yn) --

Column 11,
Line 49, delete "fuimarate" and replace with -- fumarate --

Column 16,
Line 30, delete

" 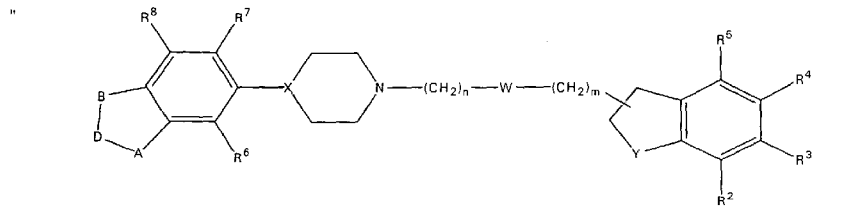 "

and replace with

-- 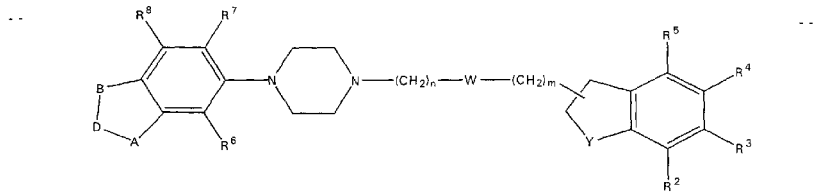 --

Column 17,
Lines 4-5, delete "$C_{16}$ alkylsulfonyl" and replace with -- $C_{1-6}$ alkylsulfonyl --

Signed and Sealed this

Eleventh Day of March, 2003

JAMES E. ROGAN
*Director of the United States Patent and Trademark Office*